(12) United States Patent
Wilson et al.

(10) Patent No.: US 11,951,029 B1
(45) Date of Patent: Apr. 9, 2024

(54) FLEXIBLE RECEPTACLES AND FLEXIBLE CONDUITS FOR BODILY FLUIDS

(71) Applicants: Taylor P. Wilson, North Augusta, SC (US); Jozef Bicerano, Savannah, GA (US)

(72) Inventors: Taylor P. Wilson, North Augusta, SC (US); Jozef Bicerano, Savannah, GA (US)

( * ) Notice: Subject to any disclaimer, the term of this patent is extended or adjusted under 35 U.S.C. 154(b) by 0 days.

(21) Appl. No.: 18/104,393

(22) Filed: Feb. 1, 2023

Related U.S. Application Data (62) Division of application No. 16/941,830, filed on Jul. 29, 2020, now abandoned.

(60) Provisional application No. 62/879,640, filed on Jul. 29, 2019.

(51) Int. Cl.
*A61F 5/455* (2006.01)
*A61F 5/44* (2006.01)
*A61F 5/453* (2006.01)

(52) U.S. Cl.
CPC ............ *A61F 5/455* (2013.01); *A61F 5/4407* (2013.01); *A61F 5/453* (2013.01)

(58) Field of Classification Search
CPC ......... A61F 5/455; A61F 5/4407; A61F 5/453
See application file for complete search history.

(56) References Cited

U.S. PATENT DOCUMENTS

| 39,641,111 | | 6/1976 | Packer | |
|---|---|---|---|---|
| 4,496,355 A | * | 1/1985 | Hall | A61F 5/455 604/327 |
| 4,500,314 A | | 2/1985 | Brendling | |
| 4,696,067 A | | 9/1987 | Woodward | |
| 4,846,819 A | * | 7/1989 | Welch | A61F 5/455 604/336 |
| 4,904,248 A | * | 2/1990 | Vaillancourt | A61F 5/455 604/327 |
| 4,963,137 A | | 10/1990 | Heyden | |

(Continued)

OTHER PUBLICATIONS

Addiction Resource, "Drug Tests 101—What Everyone Should Know About Screening", published Jul. 11, 2016; updated Jun. 24, 2019.

(Continued)

*Primary Examiner* — Benjamin J Klein
*Assistant Examiner* — Hans Kaliher
(74) *Attorney, Agent, or Firm* — Haynsworth Sinkler Boyd, P.A.

(57) ABSTRACT

Flexible receptacles and flexible conduits for bodily fluids are disclosed. The receptacles and conduits provide comfortable, user-friendly unisex flexible bodily waste collection systems that improve the accuracy and convenience when collecting urine streams from female users. One bodily waste collection system may include a cup, a bowl, a tube, a pipe, a fitting, a valve, or any combination thereof. A flexible receptacle or conduit includes an open top defined by a flexible annular rim, a base, and flexible sidewalls extending between the top and base. The flexible receptacle is a urine collection cup having an annular rim. The rim is deformable to an elliptical shape when pressure is applied there against (for example, by squeezing), thereby allowing the rim to fit between the labia majora and minora of the user.

5 Claims, 10 Drawing Sheets

(56) References Cited

U.S. PATENT DOCUMENTS

| | | | |
|---|---|---|---|
| 5,056,932 A * | 10/1991 | Young | A61J 19/00 |
| | | | 383/44 |
| 5,125,118 A | 6/1992 | Green | |
| 5,356,398 A * | 10/1994 | Willis | A61G 9/006 |
| | | | 600/573 |
| 7,347,623 B2 | 3/2008 | Cawley | |
| 8,104,960 B2 * | 1/2012 | Gill | B65F 1/0006 |
| | | | 383/44 |
| 8,298,202 B2 | 10/2012 | MCray | |
| 8,333,296 B1 | 12/2012 | Fung | |
| 8,847,001 B2 | 9/2014 | Huckfeldt et al. | |
| 9,694,938 B2 | 7/2017 | Hollis et al. | |
| 2007/0270716 A1 | 11/2007 | Wu et al. | |
| 2015/0000027 A1 | 1/2015 | Hughes et al. | |
| 2017/0325788 A1 * | 11/2017 | Ealovega | A61F 5/4553 |
| 2018/0311069 A1 | 11/2018 | Hjorth et al. | |
| 2019/0388265 A1 | 12/2019 | Brun et al. | |
| 2020/0060865 A1 | 2/2020 | Hwang | |
| 2020/0085610 A1 * | 3/2020 | Cohn | A61F 5/4408 |

OTHER PUBLICATIONS

Astm D6866-18, "Standard Test Methods for Determining the Biobased Content of Solid, Liquid, and Gaseous Samples Using Radiocarbon Analysis", 2018, ASTM International.

Astm D790-17, "Standard Test Methods for Flexural Properties of Unreinforced and Reinforced Plastics and Electrical Insulating Materials", 2017, ASTM International.

Jozef Bicerano, "Polymer Recycling Technologies", Nov. 10, 2018, Bicerano and Associates, USA.

Jozef Bicerano, "Biobased Feedstocks", Nov. 17, 2018, Bicerano and Associates, USA.

Po-Ya Chang, Li-Nien Chien, Yuh-Feng Lin, Mai-Szu Wu, Wen-Ta Chiu, and Hung-Yi Chiou, "Risk Factors of Gender for Renal Progression in Patients with Early Chronic Kidney Disease", Medicine, (2016) 95:30 (e4203).

Ana L. Flores-Mireles, Jennifer N. Walker, Michael Caparon, and Scott J. Hultgren, "Urinary Tract Infections: Epidemiology, Mechanisms of Infection and Treatment Options", Nature Reviews Microbiology, May 2015; 13(5): pp. 269-284, USA.

Alexandra Kautzky-Willer, Jürgen Harreiter, and Giovanni Pacini, "Sex and Gender Differences in Risk, Pathophysiology and Complications of Type 2 Diabetes Mellitus", Jun. 2016; 37(3): 278-316, Endocrine Reviews.

E. Omling, A. Jarnheimer, J. Rose, J. Björk, J. G. Meara, and L. Hagander, "Population-Based Incidence Rate of Inpatient and Outpatient Surgical Procedures in a High-Income Country", 2018; 105: 86-95, British Journal of Surgery.

Health, Nutrition and Population: Population Dashboard, 2018, updated annually, The World Bank.

Mark Dewolf, 12 Stats About Working Women, Mar. 1, 2017, U.S. Department of Labor Blog.

What is a Urinary Tract Infection (UTI) in Adults?, Apr. 2019, Urology Care Foundation (the official foundation of the American Urological Association).

* cited by examiner

(Prior Art)

FLEXIBLE RECEPTACLES AND FLEXIBLE CONDUITS FOR BODILY FLUIDS

RELATED APPLICATIONS

This application a divisional application of U.S. Utility patent application Ser. No. 16/941,830, filed Jul. 29, 2020, which claims priority to U.S. Provisional Patent Application No. 62/879,640, filed on Jul. 29, 2019, the disclosure of which is hereby incorporated by reference in its entirety.

FIELD OF THE INVENTION

The present application discloses and describes unisex flexible receptacles and conduits for bodily fluids.

BACKGROUND OF THE INVENTION

A. Facts and Statistics Concerning Urinalysis

Hundreds of millions of urine specimens are collected worldwide for testing every year. The reasons for the collection of these specimens include testing in relation to various medical conditions [such as urinary tract infections (UTIs), diabetes, kidney diseases, hypertension, and liver diseases], pre-surgery preparation, pregnancy testing, and drug testing. Consequently, a large percentage of the population of the world will be asked to provide one or more urine sample(s) during their lifetimes.

Females comprise a large percentage of the patients who are asked to provide urine samples.

UTIs affect approximately 150 million people each year worldwide and being female is the most important risk factor for developing a UTI (Flores-Mireles et al., 2015). It has, in fact, been estimated by the Urology Care Foundation that, about 60% of women but only about 12% of men will have at least one UTI during their lifetime.

After adjusting for age and changes over time, the incidence rate of surgery in Sweden was 9.8% higher among females, mainly due to more surgery during their fertile years (Omling et al., 2018).

Kidney diseases are common among both sexes, with proteinuria being the main risk factor for males, poor glycemic control being the main risk factor for females, and poor blood pressure control being a shared risk factor for males and females (Chang et al., 2016).

Diabetes is also common among both males and females, and sex is a major factor affecting the onset and progression of the disease (Kautzky-Willer et al., 2016).

It can be estimated from population growth statistics posted online by the World Bank that worldwide there are, on the average, about 250 babies born per minute, and hence more than 130 million babies born per year.

Statistics posted online by the U.S. Department of Labor indicate that almost 47% of the labor force in the USA consists of women. Women also constitute a large percentage of the labor force in many other countries. Drug testing is very often conducted for employment-related reasons. It has been reported by the Addiction Resource that 90% of the 55 million drug tests performed last year (hence 49.5 million drug tests) were urine tests.

B. Devices and Systems for Urine Collection

The prior art teaches various devices and systems for urine collection. Such devices and systems include funnels used as female urination aids and other devices and systems that suffer from many shortcomings. These shortcomings include one or more of complexity of design, cumbersome use procedures, and designs suitable only for use by females (thus limiting utility by requiring other devices and systems for males).

Figure 1:
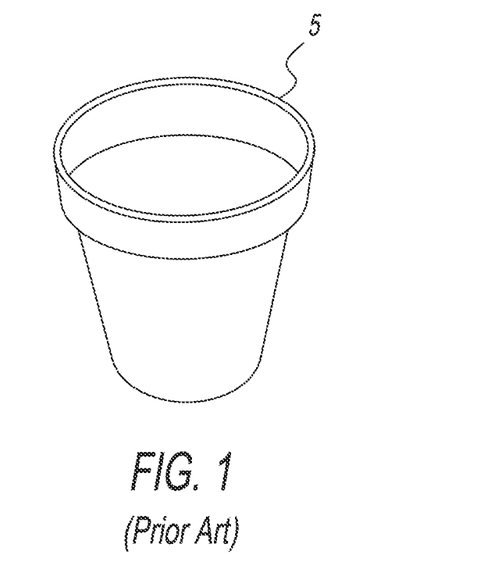
FIG. 1 illustrates a commonly used, prior art urine collection device depicted therein as a urine sample collection cup shown prior to deformation or compressional forces being applied thereto.
Figure 1A:
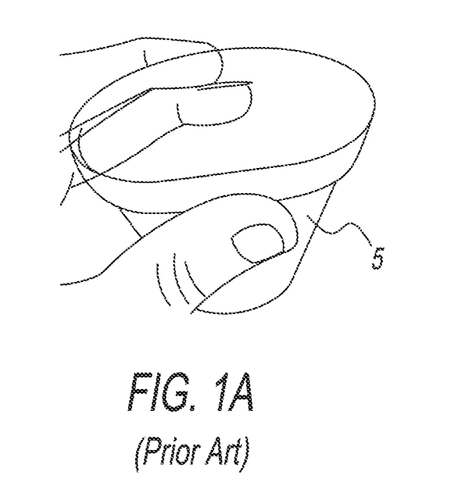
FIGS. 1A-1C illustrate in a sequential manner the effects of deforming the urine collection cup in FIG. 1.
Figure 1B:
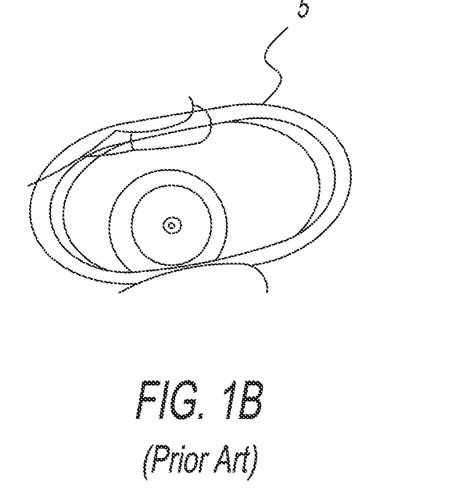
Figure 1C:
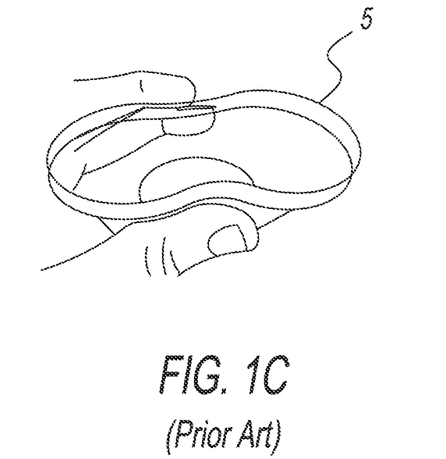
Figure 1D:
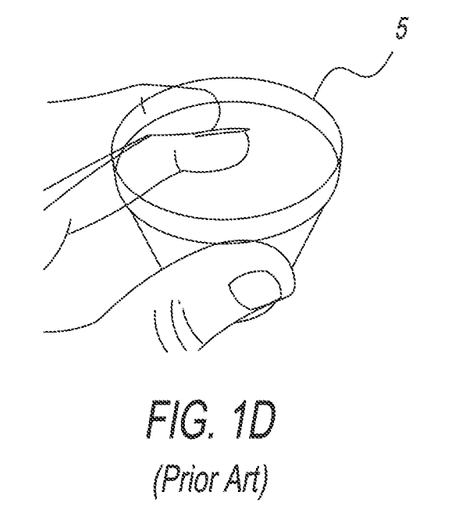
FIG. 1D shows the cup in FIGS. 1-1C back in its original shape after the previously applied pressure has been released.

The simplest and most commonly used urine collection device is a sample collection cup 5, as illustrated in FIG. 1. FIGS. 1A-1D show what happens when a standard commercially-available urine collection cup 5 purchased from the Amazon□ website is deformed. FIG. 1 shows the cup 5 in a resting position, or before any applied deformation or compressive force. FIGS. 1A-1C show what happens when increasing amounts of pressure are applied to the upper portion of the cup 5. The cup 5 was difficult to squeeze. Most importantly, it can be seen from FIG. 1C that the top of the cup 5 bends—rather than retaining an elliptical shape. The fact that the cup 5 bends rather than retaining an elliptical shape means that it lacks the ability to fit comfortably and tightly between the labia majora and minora of the user. FIG. 1D shows the cup 5 back in its original shape after the pressure has been released. Depending on the extent of deformation, stress lines also begin to form in some cups when they are deformed.

Figure 2:
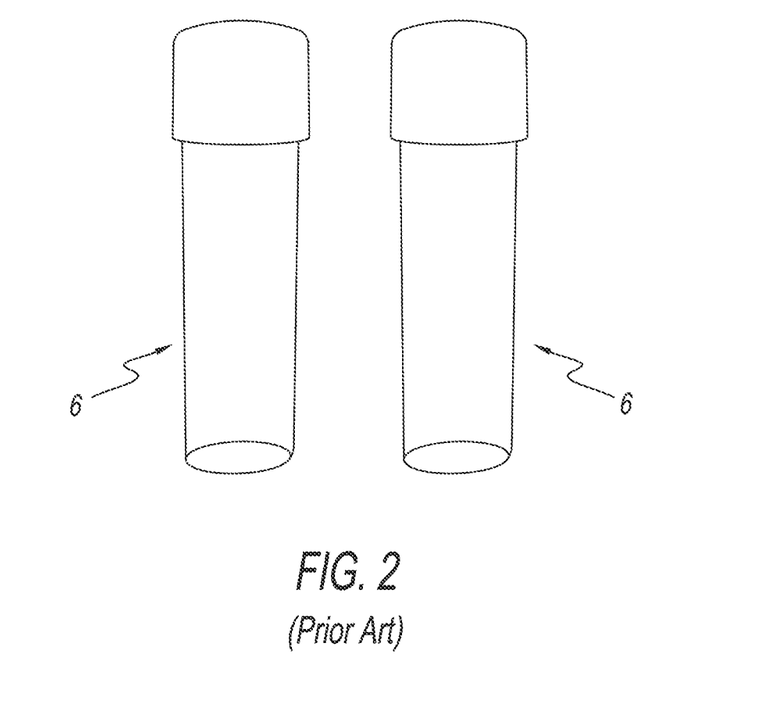
FIGS. 2-2B show various prior art test tubes used for urine collection, storage, and/or removal of a portion of a larger urine sample, such as from a conventional urine collection cup, for use in one or more tests.
Figure 2A:
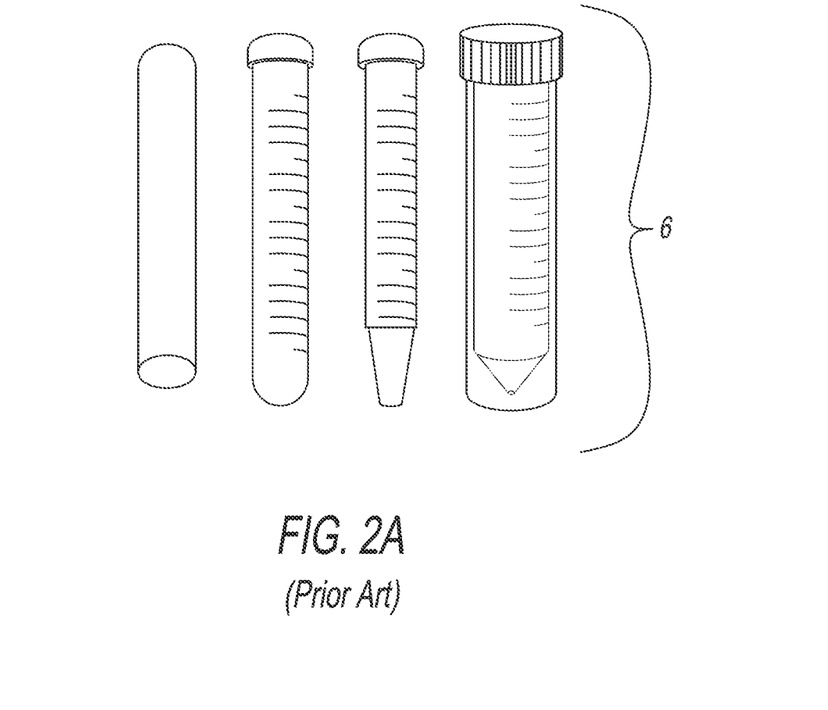
Figure 2B:
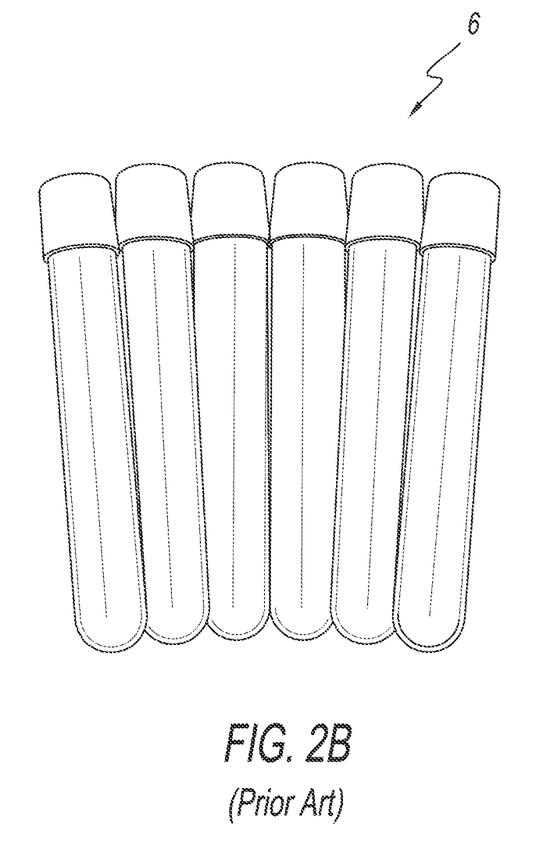

In reference to FIGS. 2-2B, exemplary prior art commercially-available test tubes 6 are depicted. A test tube 6 is sometimes used as a device for urine collection, storage, and/or removal of a portion of a larger urine sample from a urine collection cup for use in a test.

For the foregoing reasons, there is a need for unisex flexible bodily waste collection devices and systems, and especially receptacles, which can improve the convenience and comfort of urine collection from and the accuracy of urine streams collected from females while also being suitable for use by males.

A search of the prior art did not disclose any patents that read directly on the claims of the instant invention; however, the following references were considered related:

U.S. Pat. No. 3,964,111, issued in the name of Packer, Paul R.;
U.S. Pat. No. 4,500,314, issued in the name of Brendling, Lennart I.;
U.S. Pat. No. 4,696,067, issued in the name of Woodward, Marylou;
U.S. Pat. No. 4,963,137, issued in the name of Heyden, Eugene L.;
U.S. Pat. No. 5,125,118, issued in the name of Green, Edwin J.;
U.S. Pat. No. 7,347,623, issued in the name of Cawley, John;
U.S. Pat. No. 8,298,202, issued in the name of McCray, Risa Culp;
U.S. Pat. No. 8,333,296, issued in the name of Fung, Duncan C.;
U.S. Pat. No. 8,847,001, issued in the name of Huckfeldt et al.;
U.S. Pat. No. 9,694,938, issued in the name of Hollis et al.;
U.S. Patent Application no. 2007/0270716 A1, published in the name of Wu et al.;
U.S. Patent Application no. 2015/0000027, published in the name of Hughes et al.;
U.S. Patent Application no. 2018/0311069, published in the name of Hjorth et al.;
U.S. Patent Application no. 2019/0388265, published in the name of Brun et al.; and
U.S. Patent Application no. 2020/00060865, published in the name of Hwang, Ryong.

Accordingly, there is a need for unisex flexible bodily waste collection devices and systems, particularly receptacles, adapted and configured to improve both the convenience and comfort of urine collection, and the accuracy of urine streams collected from females and males.

This application presents claims and embodiments that fulfill a need or needs not yet satisfied by the products, inventions and methods previously or presently available. In particular, the claims and embodiments disclosed herein describe a unisex flexible urine collection receptacle, the receptacle comprises an open top defined by a flexible annular rim or a flexible elliptical rim, a base, and flexible sidewalls extending between the rim and the base; wherein the receptacle retaining its initial annular or elliptical shape unless pressure is applied to it and having the ability to fit between the labia majora and minora of a female user either after its flexible annular rim is deformed to elliptical shape or in its initial elliptical shape; and wherein the urine collection receptacle of the present invention providing unanticipated and nonobvious combination of features distinguished from the devices, apparatuses, inventions and methods preexisting in the art. The applicants are unaware of any device, apparatus, method, disclosure or reference that discloses the features of the claims and embodiments disclosed herein, and as more fully described below.

SUMMARY OF THE INVENTION

The present invention relates to flexible receptacles and flexible conduits for bodily fluids, satisfying the need for unisex flexible bodily waste collection systems to improve the accuracy and convenience of collection of urine streams from female users. In accordance with one embodiment of the present invention, a flexible unisex urine collection receptacle comprises an open top defined by a flexible annular rim or a flexible elliptical rim, a base, and flexible sidewalls extending between the rim and the base; and the receptacle retains its initial annular or elliptical shape unless pressure is applied to it and has the ability to fit between the labia majora and minora of a female user either after its flexible annular rim is deformed to elliptical shape or in its initial elliptical shape.

In accordance with another embodiment, a method for urine collection from a female user comprises the user: (a) placing between her thighs a flexible urine collection receptacle comprising an open top defined by a flexible annular rim, a base, and flexible sidewalls extending between the rim and the base, with the receptacle retaining its initial shape unless pressure is applied to it; (b) deforming the annular rim into an elliptical shape by applying a first pressure to the rim, to the sidewalls, or a combination thereof, wherein the first pressure is applied by squeezing with one hand, by squeezing with both hands, by squeezing between the thighs, or a combination thereof; (c) fitting the deformed elliptical rim between her labia majora and minora; (d) discharging urine into the receptacle; and (e) removing the receptacle from between her labia majora and minora.

In accordance to another embodiment, a method for urine collection from a female user comprises the user: (a) placing between her thighs a flexible urine collection receptacle comprising an open top defined by a flexible elliptical rim, a base, and flexible sidewalls extending between the rim and the base, with the receptacle retaining its initial shape unless pressure is applied to it; (b) optionally deforming the elliptical rim further by applying pressure to the rim, to the sidewalls, or a combination thereof, wherein the pressure is applied by squeezing with one hand, by squeezing with both hands, by squeezing between the thighs, or a combination thereof; (c) fitting the elliptical rim between her labia majora and minora; (d) discharging urine into the receptacle; and (e) removing the receptacle from between her labia majora and minora.

Selected embodiments of the invention will be described in greater detail hereinbelow. These embodiments are intended to facilitate the teaching of the invention by presenting specific examples of how it may be implemented, without limiting the scope of the invention.

DESCRIPTION OF THE EMBODIMENT(S)

A. Flexible Receptacles and Flexible Conduits

The present invention relates to flexible receptacles and flexible conduits for bodily fluids, satisfying the need for unisex flexible bodily waste collection systems to improve the accuracy and convenience of collection of urine streams from female users. Cups, bowls, tubes, pipes, fittings, valves, and any combinations thereof, are non-limiting examples of flexible receptacles and flexible conduits.

FIG. 1 illustrates a conventional, prior art urine sample collection cup 5 shown prior to deformation or compressional forces being applied thereto. The effects of applying increasing amounts of pressure to an upper portion of such conventional urine collection cup 5 are clearly evident, as illustrated in FIGS. 1A-1C. The prior art cup 5 is difficult to squeeze. When compressional force is applied to the cup 5 (or the cup 5 is squeezed), such pressure causes the upper end or top of the cup 5 to bend rather than retain an elliptical shape. The fact that the cup 5 bends rather than retaining an elliptical shape means that the prior art cup 5 lacks the ability to fit comfortably and tightly between the labia majora and minora of the female user.

Figure 5:
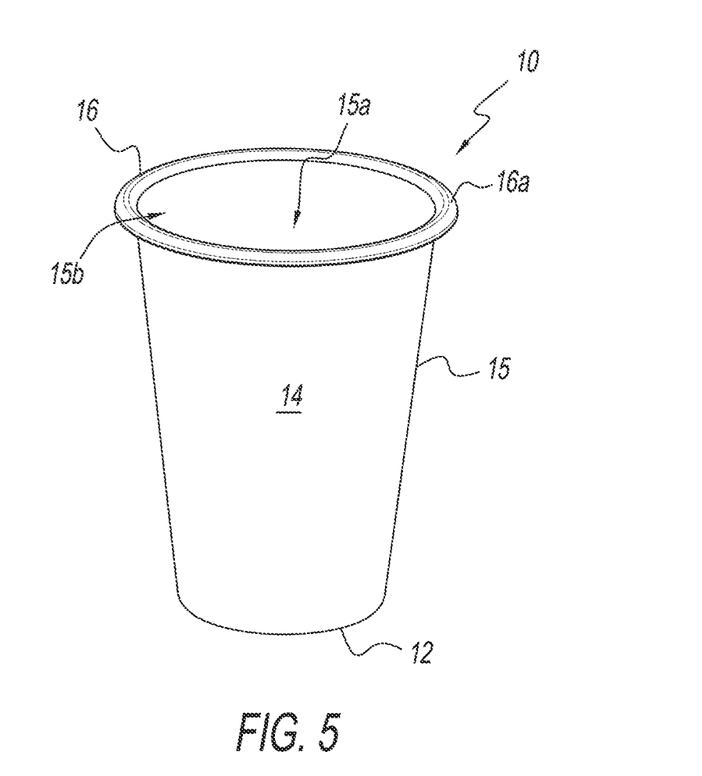
FIG. 5 is a perspective view of a urine collection receptacle, in accordance to one embodiment of the present invention.
Figure 5A:
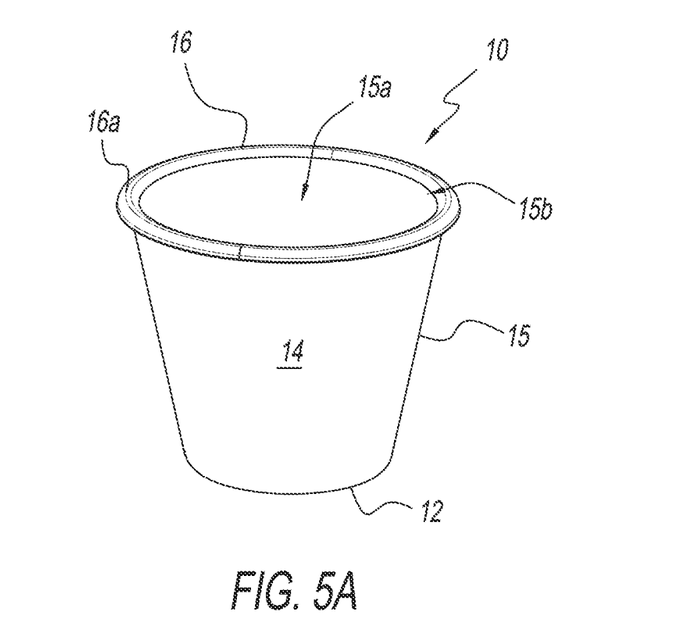
FIG. 5A is a perspective view of a urine collection receptacle, in accordance to another embodiment of the present invention.
Figure 5B:
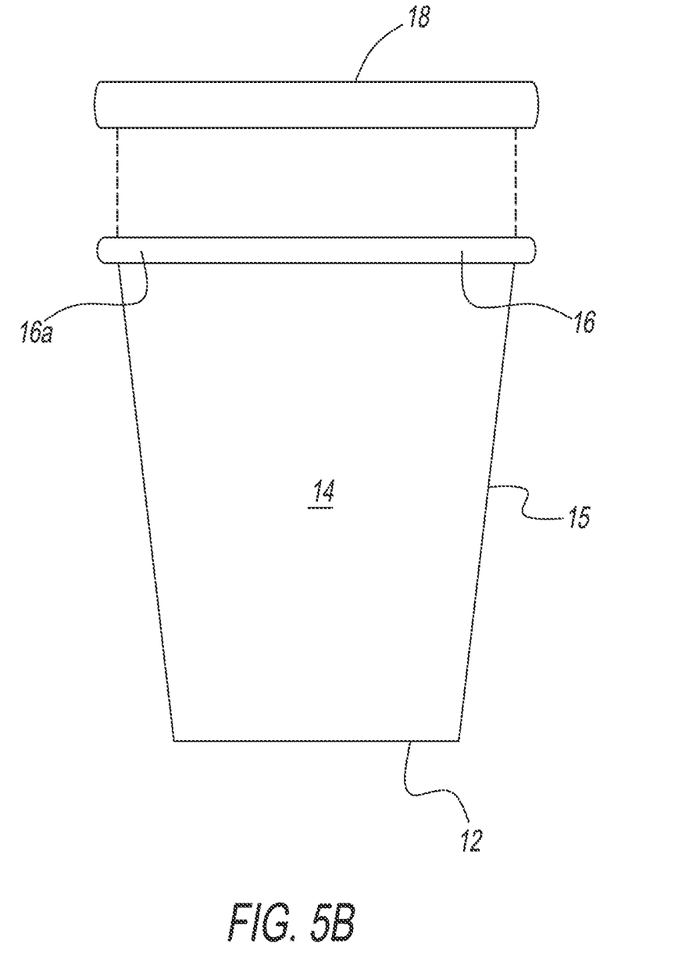
FIG. 5B is an exploded perspective view of the collection receptacle in FIG. 5 showing a lid secured to the rim thereof.
Figure 5C:
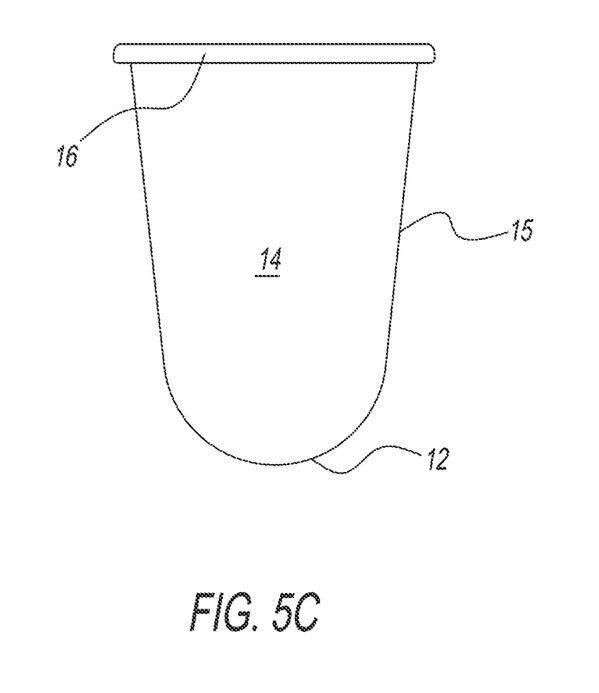
FIG. 5C is a side elevational view of a urine collection receptacle having a curved base, in accordance to an alternate embodiment of the present invention.

A unisex flexible urine collection receptacle 10 comprises a closed bottom or base 12 from which a flexible continuous sidewall 14 extends vertically therefrom integrally forming a flexible cylindrical vessel 15 having an open interior volume 15a. The cylindrical vessel 15 has an open upper end 15b comprising a flexible, bulbous rim 16 or lip. Although the rim 16 may comprise a planar or flat upper surface, the bulbous rim 16 is preferably curved, as shown in FIGS. 5-5C. The open upper end 15b of the cylindrical vessel 15 provides direct open passage into the open interior volume 15a thereof. The flexible, bulbous rim 16 or lip may comprise one of many geometric shapes and configurations, such as including, but not limited to, annular, circular, elliptical, and oval. Likewise, the continuous sidewall 14 or cylindrical vessel 15 may comprise one of many geometric shapes and configurations, such as including, but not limited to, annular, circular, elliptical, and oval. It is further envisioned the cylindrical vessel 15 may comprise a generally, conical configuration comprising an elliptical or oval cross-sectional shape, and integral flexible rim 16 corresponding respectively thereto in cross-sectional shape. More specifically in reference to a generally, conical configuration, the flexible urine collection receptacle 10 tapers inward from a greater transverse width at the flexible rim 16 to a smaller transverse width at the closed base 12. It is also envisioned the cylindrical vessel 15 may comprise a generally, conical configuration comprising an annular cross-sectional shape, as depicted by the collection receptacle 10 embodiment illustrated in FIG. 5.

The rim 16 is initially annular in shape. The rim 16 flexibly changes to an elliptical shape when pressure is applied, as happens for example when a female user squeezes the vessel 15 with her hands. The elliptical shape of the rim 16 provides ability to fit the vessel 15 between the labia majora and minora of the user, thereby improving the accuracy of the urine stream. The vessel 15 is easy to squeeze so that users can easily adjust the size of the rim 16 to provide the best fit, but it is not collapsible. The rim 16 locks into and remains in this elliptical shape when the user releases the pressure, making it unnecessary for the user to maintain the pressure while urinating. The rim 16 returns from this locked-in elliptical shape to its original annular shape when pressure is applied (the rim 16 is squeezed again) to allow placement of a lid 18 on the vessel 15 if desired.

In accordance to one embodiment, the vessel 15 is constructed of a pliable material and therefore retains its initial shape unless pressure is applied to it and has the ability to fit between the labia majora and minora of a female user either after its flexible annular rim 16 is deformed to elliptical shape or in an initial resting state regarding elliptically-shaped rim 15 embodiments. A cup 5 and a tube 6 are non-limiting examples of receptacles that are often utilized for urine collection, storage, and/or removal of a portion of a larger urine sample from a urine collection cup for use in a test.

In some non-limiting embodiments, a female user can deform the annular rim 16 of the vessel 15 into an elliptical shape by applying a first pressure to the rim 16, to the sidewall 14, or a combination thereof. Without limiting the generality of the invention, this first pressure is often applied by squeezing with one hand, by squeezing with both hands, by squeezing between the thighs, or a combination thereof.

Figure 3:
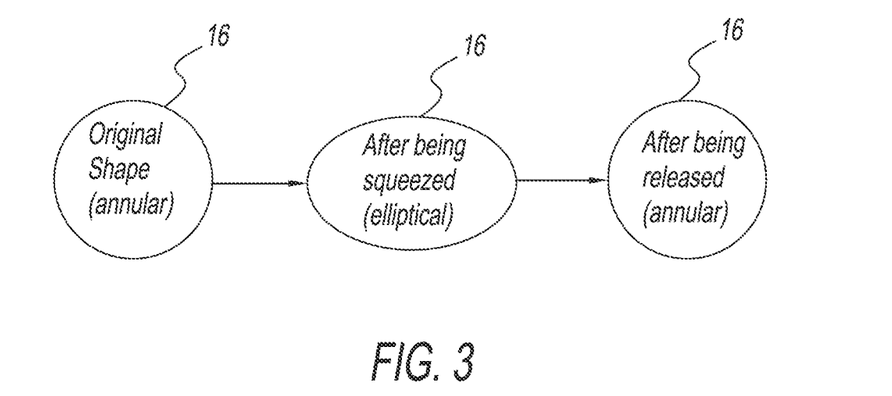
FIG. 3 illustrates a flow diagram depicting the changes to the shape of the rim of a unisex flexible urine collection receptacle as pressure is applied and thereafter relaxed, in accordance to one embodiment of the present invention.

In accordance to another embodiment depicted in FIG. 3, the cylindrical vessel 15 is constructed of a returnably-resilient material. In some non-limiting examples of embodiments of this general type, the rim 16 returns from its deformed elliptical shape to its original annular shape upon releasing the first pressure. For example, FIG. 3 shows the shape of the rim 16 of a urine collection receptacle 10 in some such embodiments. The rim 16 is initially annular in shape. It changes to an elliptical shape when pressure is applied, as happens for example when a female user squeezes the receptacle 10 with her hands. The elliptical shape of the rim 16 of the receptacle 10 provides ability to fit the rim 16 of the cylindrical vessel 15, and thus the upper portion of the collection receptacle 10 between the labia majora and minora of the user, thereby improving the accuracy of the urine stream. The urine collection receptacle 10 is easy to squeeze so that users can easily adjust the size of the rim 16 to provide the best fit, but it is not collapsible. The rim 16 returns to an annular shape when the pressure is released so that a lid 18 can be placed on the receptacle 10 if desired.

Figure 4:
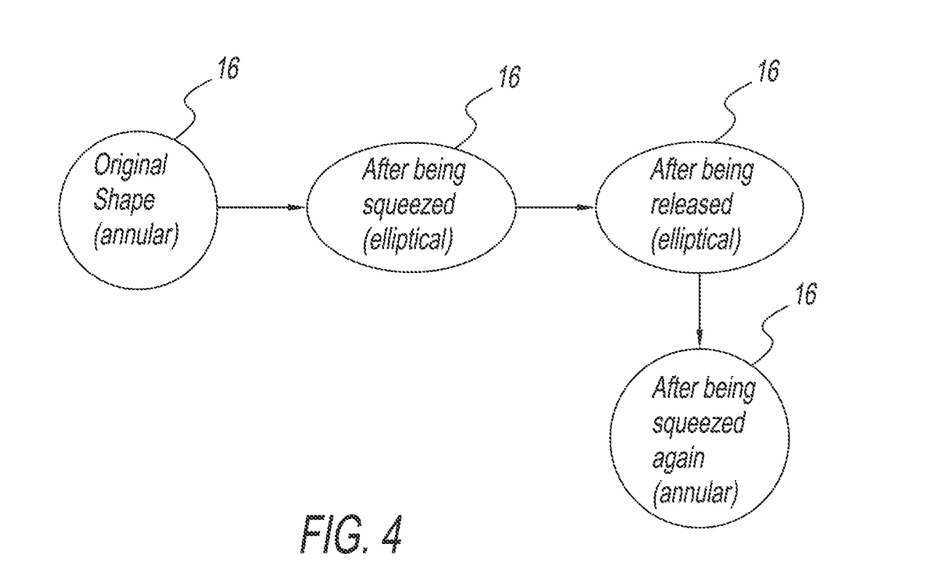
FIG. 4 illustrates a flow diagram depicting the changes to the shape of the rim of a unisex flexible urine collection receptacle as pressure is applied, removed, and again applied, in accordance to another embodiment of the present invention.

In accordance to another embodiment depicted in FIG. 4, the cylindrical vessel 15 is constructed of a pliable material. In some other non-limiting examples of embodiments of this general type, the rim 16 remains locked in its deformed elliptical shape upon releasing the first pressure, but it can optionally be returned from its locked elliptical shape to an annular shape upon applying a second pressure (such as, for example compressional). Without limiting the generality of the invention, this second pressure is often applied by squeezing with one hand, by squeezing with both hands, by squeezing between the thighs, or a combination thereof. For example, FIG. 4 shows the shape of the rim 16 of a urine collection receptacle 10 in some embodiments of the invention. The rim 16 is initially annular in shape. It changes to an elliptical shape when pressure is applied, as happens for example when a female user squeezes the receptacle 10 with her hands. The elliptical shape of the rim 16 provides ability to fit the rim 16 of the cylindrical vessel 15, and thus the upper portion of the collection receptacle 10 between the labia majora and minora of the user, thereby improving the accuracy of the urine stream. The urine collection receptacle 10 is easy to squeeze so that users can easily adjust the size of the rim 16 to provide the best fit, but it is not collapsible. The rim 16 locks into and remains in this elliptical shape when the user releases the pressure, making it unnecessary for the user to maintain the pressure while urinating. The rim 16 returns from this locked-in elliptical shape to its original annular shape when pressure is reapplied (the rim 16 is squeezed again) so that a lid 18 can be placed on the receptacle 10 if desired.

As previously described, in accordance to one embodiment, the rim 16 of the receptacle 10 may comprise a flat or planar shape. Preferably, the rim 16 of the receptacle 10 has a rounded lip 16a in some other embodiments to enhance comfort when it touches the skin. FIGS. 5 and 5A show two urine collection receptacles 10 of different sizes and shapes both having a rim 16 comprising a rounded or curved lip 16a.

The base 12 of the vessel 15 is curved in some embodiments. The base 12 of the vessel 15 is flat in some other embodiments so that the vessel 15 can be placed on a flat surface in an upright orientation.

A lid 18 may optionally be placed on a receptacle 10 of the invention after collecting a sample of urine. Any type of lid used on conventional urine sample containers may be used if the placement of a lid is desired, and the lid 18 is dimensionally-sized and configured to sufficiently close and seal the open upper end 15b of the receptacle 10.

In addition to providing significant benefits to female subjects, the flexible receptacles 10 of the invention are unisex so that they can be used by male subjects as well. The key to the versatility of the flexible receptacles 10 of the invention is the fact that they retain their initial shape unless pressure is applied to deform them. A female subject can apply pressure to deform a urine collection receptacle 10 so that it fits between her labia majora and minora. On the other hand, a male subject can use it in its original shape, in the same way as he would use a conventional rigid urine collection cup. This versatility is one of the major advantages of the flexible receptacles 10 of the invention over prior art female urination aids. A urinalysis laboratory would need to purchase and keep in stock both prior art female urination aids for use by female subjects and rigid urine collection cups for male subjects. By contrast, it would only need to purchase and keep in stock flexible receptacles 10 of the present invention for use by both female subjects and male subjects.

B. Understanding and Quantification of Flexibility

The receptacle must have sufficient flexibility to be deformable from having an annular rim 16 to having an elliptical rim 16 without bending, cracking, and/or stress line formation. On the other hand, the receptacle 10 must not be extremely flexible since it may then tend to deform (for example, collapse under its own weight) even without any applied pressure rather than retaining its initial shape unless pressure is applied to it. Without limiting the scope of the invention, we note that the terms "semiflexible" and "semirigid" are often used by scientists and engineers in describing articles that manifest such flexibility characteristics.

The flexibility of a receptacle depends on the inherent flexibility of its material of construction, on its thickness, and on its detailed shape. It is often helpful, during product design, to compare the inherent flexibilities of candidate materials by using test specimens of identical thickness and shape for all materials. Any suitable testing method may be used for making such comparisons. A useful non-limiting example is the measurement of the flexural moduli of candidate materials according to ASTM D790, "Standard Test Methods for Flexural Properties of Unreinforced and Reinforced Plastics and Electrical Insulating Materials". In practice, if off-the-shelf commercial materials of construction are being considered, a flexural modulus measured according to ASTM D790 will often be listed on the technical datasheets of each of the materials of interest.

C. Thermoplastic Polymers and Fabrication Processes

The material of construction of a receptacle of the invention comprises a thermoplastic polymer in some embodiments. Any suitable thermoplastic polymer may be used.

The material of construction of the receptacle comprises a blend of two or more thermoplastic polymers in some other embodiments. Any suitable thermoplastic polymers may be used as blend components. Without limiting the generality of the invention, one such approach is to flexibilize a rigid thermoplastic polymer which commonly being used in receptacles manufactured according to prior art by blending into it a quantity of thermoplastic elastomer sufficient to impart the desired flexibility characteristics.

When comparing different thermoplastic elastomers that can be blended with comparable ease into a given rigid polymer, the same percentage of the thermoplastic elastomer will tend to provide greater flexibilization with increasing ratio RFM defined by a flexural modulus of the least flexible polymer divided by a flexural modulus of the most flexible polymer included in the blend, measured according to ASTM D790. Without limiting the generality of the invention, RFM is at least 10 in some embodiments and at least 20 in a subset of such embodiments.

Thermoplastic polymers used in blends differ in their relative compatibilities. For example, some pairs of thermoplastic polymers are sufficiently compatible to allow the dry blending of their pellets followed by the melt processing of the resulting dry blend to obtain a fabricated article of excellent quality. Some other pairs of thermoplastic polymers are not compatible enough for dry blending to provide acceptable fabricated articles, and hence must be melted and then blended in the melt state prior to fabricating an article of excellent quality from the melt. Without limiting the generality of the invention, in some embodiments the disadvantages in terms of increased process complexity and process cost of needing to use a melt blending step may be used as a selection criterion in seeking thermoplastic elastomers sufficiently compatible with the rigid polymer needing flexibilization to allow the use of dry blending.

Any suitable fabrication method may be used to manufacture a receptacle of the invention from thermoplastic polymers and thermoplastic polymer blends. Injection molding, thermoforming, blow molding, compression molding, and rotational molding, are non-limiting examples of manufacturing methods that may be used. Without limiting the generality of the invention, it is noted that injection molding, thermoforming, and blow molding are the fabrication methods that are most commonly used for manufacturing cups from thermoplastic polymers.

Thermoplastic polymers used in manufacturing various types of receptacles include polypropylene, high-density polyethylene, low-density polyethylene, linear low-density polyethylene, poly(ethylene terephthalate), glycol-modified poly(ethylene terephthalate), high-impact polystyrene, cyclic olefin copolymers, and poly(lactic acid), and polyhydroxyalkanoates. Some non-limiting examples of the invention use flexible grades or flexibilized versions of these polymers in manufacturing receptacles.

The following non-limiting examples are helpful in understanding thermoplastic embodiments. ExxonMobil Chemical Company has developed many polypropylene product grades, as well as many thermoplastic elastomer product grades based on modifications of polypropylene and hence sufficiently compatible with polypropylene to obtain fabricated articles of excellent quality after dry blending of the pellets of the polypropylene and the thermoplastic elastomer. Since the rheological characteristics that make a thermoplastic polymer more suitable for injection molding differ from the rheological characteristics that make a thermoplastic polymer more suitable for thermoforming, different product grades have been optimized for injection molding and for thermoforming. The combinations of polypropylene and thermoplastic elastomer product grades that were recommended by customer technical support personnel of ExxonMobil Chemical Company for use in prototyping trials are summarized in Table 1 provided hereinbelow.

TABLE 1

Combinations of polypropylene product grade and thermoplastic elastomer product grade recommended by the customer technical support personnel of ExxonMobil Chemical Company for use in prototyping trials.

| Process | PP | FM (MPa) | TPE | FM (MPa) | $R_{FM}$ |
|---------|----|----|-----|-----|------|
| TF | ExxonMobil ® PP6262 | 1710 | Vistamaxx ® 3020FL | 65.3 | 26.2 |
| TF | ExxonMobil ® PP6262 | 1710 | Vistamaxx ® 6102 | 14.4 | 118.8 |
| IM | ExxonMobil ® PP9074MED | 1050 | Vistamaxx ® 6502 | 20.4 | 51.5 |

The following abbreviations are used: TF: Thermoforming, IM: Injection molding, FM: Flexural modulus, RFM: Flexural modulus of polypropylene (PP) divided by flexural modulus of thermoplastic elastomer (TPE).

D. Thermoset Polymers and Fabrication Processes

The material of construction of a receptacle of the invention comprises a thermoset polymer in some embodiments. Any suitable thermoset polymer may be used. Without limiting the generality of the invention, suitable thermoset polymers include covalently cross-linked semiflexible rubbers and elastomers, with the term "semiflexible" being defined above.

Any suitable fabrication method may be used to manufacture a receptacle of the invention from thermoset polymers. Reaction injection molding, injection molding, thermoforming, blow molding, compression molding, rotational molding, resin transfer molding, and spin casting are non-limiting examples of manufacturing methods that may be used.

E. Use of Biobased and/or Recycled Polymers as an Option

In some non-limiting embodiments of the invention, the material of construction of a receptacle comprises (a) ingredients obtained or derived from biobased feedstocks, or (b) ingredients obtained or derived from recycled polymer wastes, or (c) combinations or mixtures thereof. Any of these families (a), (b), and (c) of embodiments generally provides a more sustainable and hence a more environmentally friendly alternative to a material of construction obtained or derived entirely from fossil fuel based virgin feedstocks.

Many plants, animals, microorganisms, and fungi are biobased feedstock sources for obtaining and/or deriving monomers, oligomers, polymers, and/or biofibers (Bicerano, 17 Nov. 2018). It is often desirable to replace non-renewable fossil fuel based polymers with renewable biobased polymers. In some instances, such replacement is only partial so that the material of construction for a product is a blend of a fossil fuel based polymer and a biobased polymer. For example, the material of construction of a receptacle may comprise at least 10%, at least 40%, or at least 70% by weight biobased content, as measured by using ASTM D6866, "Standard Test Methods for Determining the Biobased Content of Solid, Liquid, and Gaseous Samples Using Radiocarbon Analysis". In some other instances, a biobased polymer replaces a fossil fuel based polymer completely. Poly(lactic acid) and polyhydroxyalkanoates are examples of biobased polymers used in manufacturing various types of receptacles. Some non-limiting examples of the invention use flexibilized versions of these polymers in manufacturing receptacles.

Efforts to recycle post-consumer polymer products and factory scraps include both the collection of growing percentages of such polymer wastes and the development of improved recycling technologies (Bicerano, 10 Nov. 2018). There are, therefore, continuing trends both towards recycling an increasing percentage of polymer wastes and towards obtaining recycled feedstocks of improved quality that can be used to manufacture products of higher quality than was possible in the past. In some instances, the replacement is only partial so that a polymer used as the material of construction for a product contains both recycled content and virgin content. For example, at least 10%, at least 25%, or at least 40% by weight of the material of construction of a receptacle may be obtained or derived from recycled polymer wastes. In some other instances, such replacement is complete, with the material of construction of a receptacle being obtained or derived entirely from recycled polymer wastes.

F. Methods for Urine Collection

Figure 6:
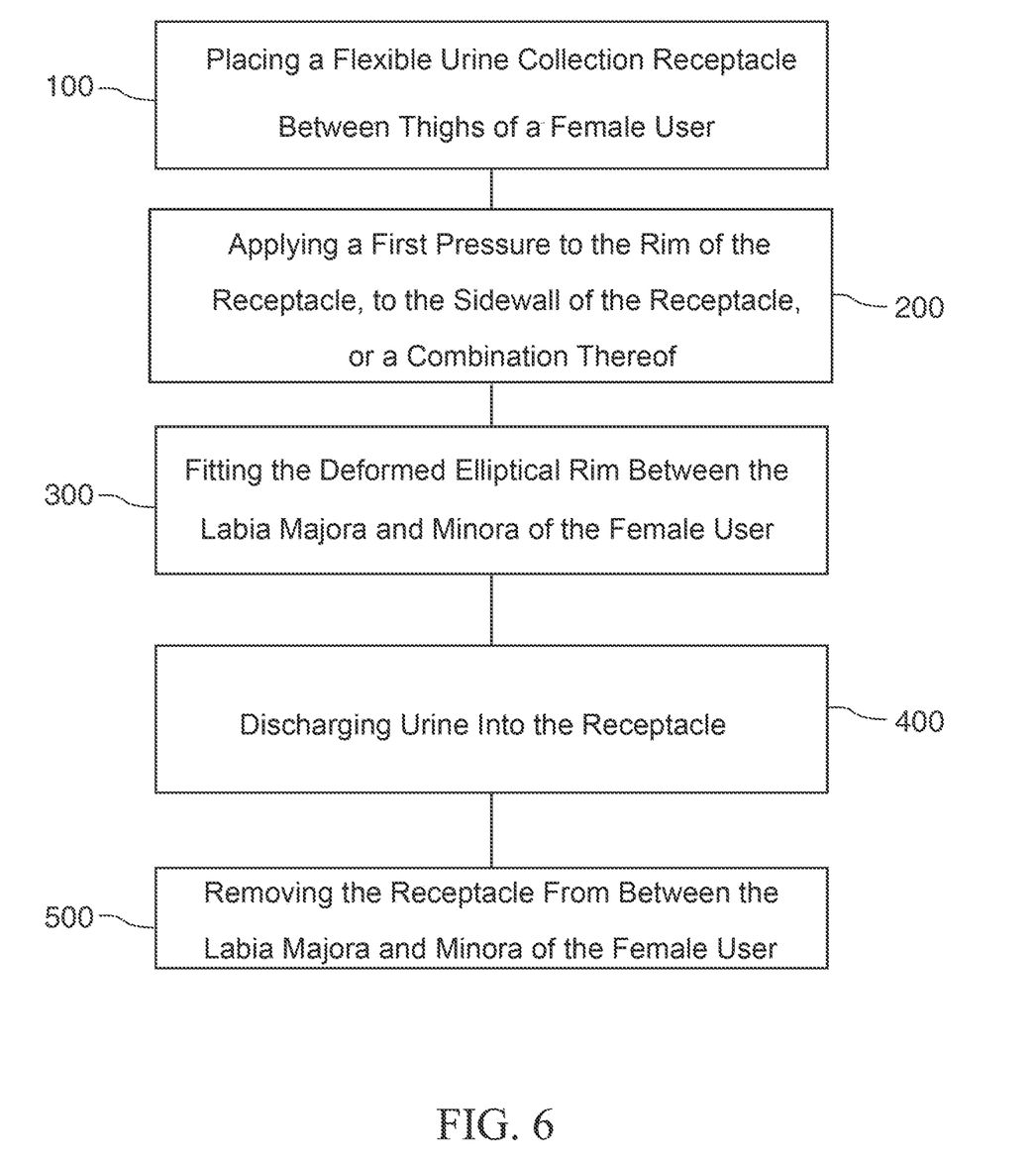
FIG. 6 is a block diagram of the general steps of a urine collection method described herein utilizing a unisex flexible urine collection receptacle.

In accordance with FIGS. 1-5C illustrating a number of embodiments for a unisex flexible urine collection receptacle 10, in another embodiment consistent with FIG. 6, a method for urine collection from a female user may be generally described as comprising the steps of: (a) placing 100 a flexible urine collection receptacle 10 between thighs of a female user, the receptacle 10 comprising an open top 15b defined by a flexible annular rim 16, a base 12, and a continuous flexible sidewall 14 extending between the rim 16 and the base 12, wherein the receptacle 10 retaining its initial shape unless pressure is applied thereto; (b) applying 200 a first pressure to the rim 16, to the sidewall 14, or a combination thereof, so as to deform the annular rim 16 into an elliptical shape, wherein the first pressure is applied by squeezing with one hand, by squeezing with both hands, by squeezing between the thighs, or a combination thereof; (c) fitting 300 the deformed elliptical rim 16 between the labia majora and minora of the female user; (d) discharging 400 urine into the receptacle 10; and (e) removing 500 the receptacle 10 from between the labia majora and minora of the female user. In some non-limiting examples of embodiments of this general type, the rim 16 returns from its deformed elliptical shape to its original annular shape upon releasing the first pressure as illustrated in FIG. 3. In some other non-limiting examples of embodiments of this general type, the rim 16 remains locked in its deformed elliptical shape upon releasing the first pressure, but it can optionally be returned from its locked in elliptical shape to an annular shape upon applying a second pressure, as illustrated in FIG. 4.

Figure 7:
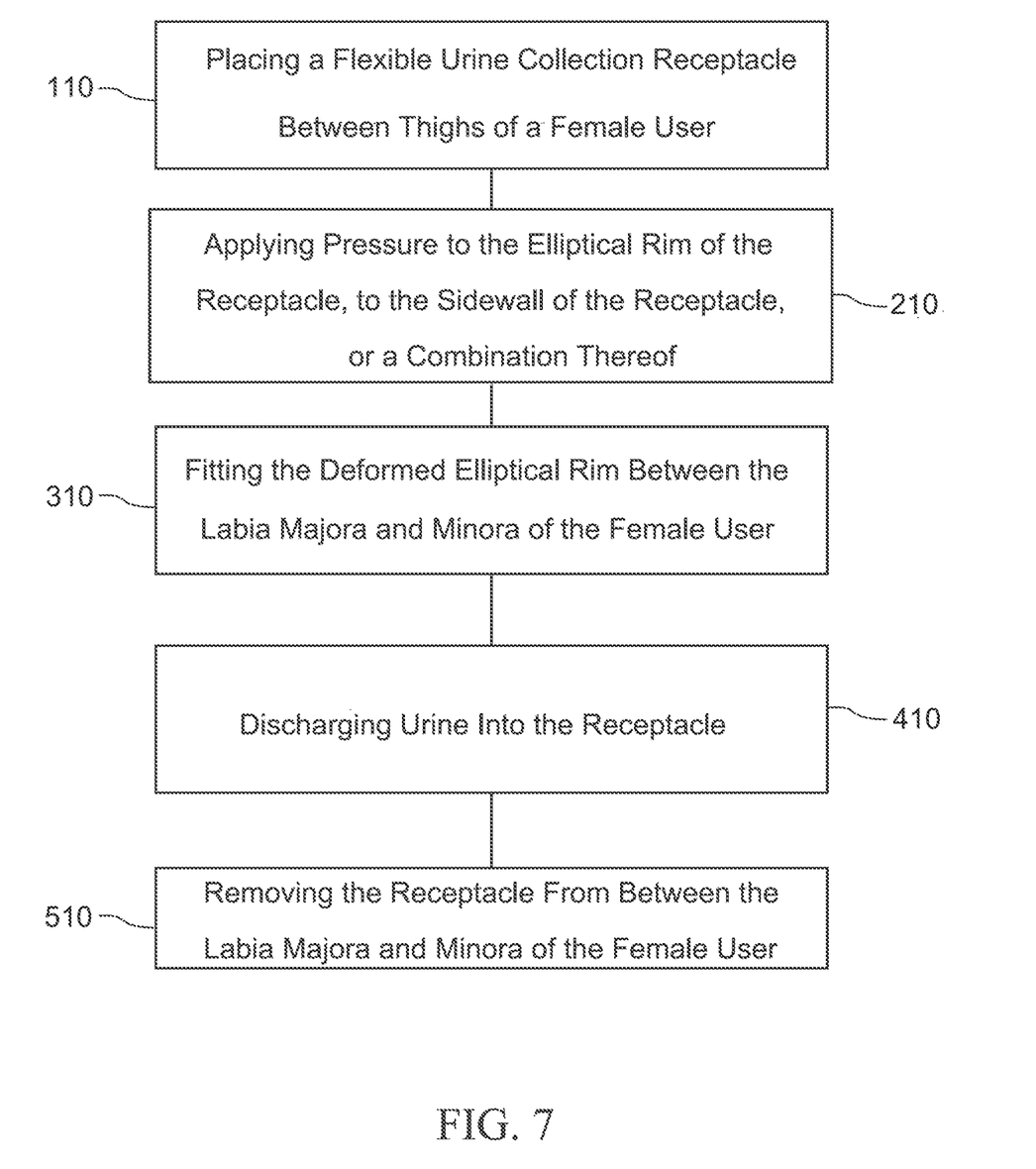
FIG. 7 is a block diagram of the general steps of a urine collection method described herein utilizing a unisex flexible urine collection receptacle, in accordance with another embodiment of the present invention.

In another embodiment consistent with FIG. 7, a method for urine collection from a female user comprises the steps of: (a) placing 110 a flexible urine collection receptacle 10 between thighs of a female user, the receptacle 10 comprising an open top 15b defined by a flexible elliptical rim 16, a base 12, and a continuous flexible sidewall 14 extending between the rim 16 and the base 12, wherein the receptacle 10 retaining its initial shape unless pressure is applied thereto; (b) optionally deforming the elliptical rim 16 further by applying pressure 210 to the elliptical rim 16, to the sidewall 14, or a combination thereof, wherein the pressure is applied by squeezing with one hand, by squeezing with both hands, by squeezing between the thighs, or a combination thereof; (c) fitting 310 the elliptical rim 16 between the labia majora and minora of the female user; (d) discharging 410 urine into the receptacle 10; and (e) removing 510 the receptacle 10 from between the labia majora and minora of the female user.

It is to be understood that the embodiments and claims are not limited in application to the details of construction and arrangement of the components set forth in the description and/or illustrated in drawings. Rather, the description and/or the drawings provide examples of the embodiments envisioned, but the claims are not limited to any particular embodiment or a preferred embodiment disclosed and/or identified in the specification. Any drawing figures that may be provided are for illustrative purposes only, and merely provide practical examples of the invention disclosed herein. Therefore, any drawing figures provided should not be viewed as restricting the scope of the claims to what is depicted.

The embodiments and claims disclosed herein are further capable of other embodiments and of being practiced and carried out in various ways, including various combinations and sub-combinations of the features described above but that may not have been explicitly disclosed in specific combinations and sub-combinations.

Accordingly, those skilled in the art will appreciate that the conception upon which the embodiments and claims are based may be readily utilized as a basis for the design of other structures, methods, and systems. In addition, it is to be understood that the phraseology and terminology employed herein are for the purposes of description and should not be regarded as limiting the claims.

What is claimed is:

1. A method for collecting urine from a female user comprising the steps of:
    placing a flexible urine collection receptacle between thighs of a female user, the receptacle comprises an open top defined by a flexible annular rim, a base, and a continuous flexible sidewall extending between the rim and the base;
    applying a pressure to the annular rim, to the sidewall, or a combination thereof, so as to deform the annular rim into an elliptical shape;
    fitting the elliptical-shaped rim between the labia majora and minora of the female user;
    discharging urine into the receptacle, the urine being retained in the receptacle; and
    removing the receptacle from between the labia majora and minora of the female user.

2. The method of claim 1, wherein the elliptical-shaped rim flexibly returns to an annular shape upon releasing of the applied pressure.

3. The method of claim 1, wherein the elliptical-shaped rim remains locked in the elliptical shape upon releasing of the applied pressure, the applied pressure being a first pressure.

4. The method of claim 3, wherein the elliptical-shaped rim returns to an annular shape upon applying a second pressure.

5. A method for collecting urine from a female user comprising the steps of:
    placing a flexible urine collection receptacle between thighs of a female user, the receptacle comprises an open top defined by a flexible elliptical rim, a base, and a continuous flexible sidewall extending between the rim and the base;
    applying a pressure to the elliptical rim, to the sidewall, or a combination thereof, so as to deform the elliptical rim;
    fitting the deformed elliptical rim between the labia majora and minora of the female user;
    discharging urine into the receptacle, the receptacle being retained in the receptacle; and
    removing the receptacle from between the labia majora and minora of the female user.

\* \* \* \* \*